United States Patent [19]

Thompson

[11] 4,295,214
[45] Oct. 13, 1981

[54] ULTRASONIC SHEAR WAVE TRANSDUCER

[75] Inventor: Robert B. Thompson, Thousands Oaks, Calif.

[73] Assignee: Rockwell International Corporation, El Segundo, Calif.

[21] Appl. No.: 68,988

[22] Filed: Aug. 23, 1979

[51] Int. Cl.$^3$ .............................................. G01N 29/04
[52] U.S. Cl. ...................................... 367/140; 73/668; 73/779
[58] Field of Search .................. 73/640, 643, 668, 779; 324/233, 232; 367/140, 149, 156, 168

[56] References Cited

U.S. PATENT DOCUMENTS

| | | |
|---|---|---|
| 3,550,435 | 12/1970 | Kaule ..................................... 73/643 |
| 3,555,887 | 1/1976 | Wood ..................................... 73/643 |
| 3,697,867 | 10/1972 | Kleesattel .............................. 73/643 |
| 3,850,028 | 11/1974 | Thompson et al. .................... 73/640 |
| 4,048,847 | 9/1977 | Alers et al. ............................ 73/779 |
| 4,058,002 | 11/1977 | Moran ................................... 73/643 |
| 4,080,836 | 3/1978 | Thompson et al. .................... 73/643 |
| 4,092,868 | 6/1978 | Thompson et al. .................... 73/638 |
| 4,100,809 | 7/1978 | Babrev et al. ......................... 73/643 |
| 4,127,035 | 11/1978 | Vasile ................................... 73/629 |

FOREIGN PATENT DOCUMENTS

| | | | |
|---|---|---|---|
| 969515 | 9/1964 | United Kingdom ................. 73/668 |
| 376127 | 5/1973 | U.S.S.R. ............................. 73/643 |
| 532048 | 10/1976 | U.S.S.R. ............................. 73/643 |

OTHER PUBLICATIONS

Vasile et al., "Periodic Magnet . . . Application," 1977, pp. 84–88, Ultrasonics Symp. Phoenix, 1977.
Thompson, "Noncontact Transducers", 1977, pp. 74–83, 1777 Ultrasonics Symp.
Thompson, "Mechanisms of Electromagnetic . . . Polycrystal", 12/77, J. Appl. Phys., vol. 48, #12.

Primary Examiner—Nelson Moskowitz
Attorney, Agent, or Firm—H. Fredrick Hamann; Craig O. Malin; John J. Deinken

[57] ABSTRACT

Disclosed is an electromagnetic acoustic transducer, including an electrical conductor adapted to carry an alternating current in a current plane, the current being conveyed by the conductor in uniformly spaced, parallel, and alternate directions at any instant, and a source of magnetic flux positioned to direct a static magnetic field parallel to the alternate directions, the transducer thereby being adapted to generate or detect a horizontally polarized shear wave in a ferromagnetic material. The transducer may be made unidirectional by adding a second electrical conductor adapted to carry a second alternating current 90° out of phase with respect to the first alternating current in a second current plane substantially coplanar with the first current plane, the second current being carried by the second conductor at any instant in parallel and alternate directions spaced by the same uniform amount, the second conductor being parallel to but staggered from the first conductor by half of the uniform amount.

9 Claims, 4 Drawing Figures

ULTRASONIC SHEAR WAVE TRANSDUCER

BACKGROUND OF THE INVENTION

This invention is concerned with the field of nondestructive testing and, more particularly, with the use of ultrasonic waves in nondestructive testing.

Nondestructive testing is a branch of materials science which is concerned with all aspects of quality and uniformity in materials. Ultrasonic techniques have proven to be a useful tool in a variety of nondestructive testing measurement tasks, covering all phases of testing. At the research and development stage, for example, ultrasonics may be utilized to identify material variables. In addition, ultrasonic techniques may advantageously be applied as a quality control measure during production, in process controls designed to ensure the uniformity of a continuously produced product, and as a part of on-site inspections of installed systems. Finally, ultrasonic testing systems are increasingly being applied to examine in-service components to detect failure parameters, such as wear, deterioration, corrosion, etc.

Within the area of ultrasonics, a number of different types of wave energy may be utilized. Longitudinal waves, Rayleigh waves, and shear waves (polarized horizontally, vertically, or angularly) will propagate in an elastic material. In a bounded medium, such as a plate, ultrasonic waves will travel in the form of guided waves, a phenomenon which is analogous to the transmission of microwaves in a waveguide. Horizontally polarized shear waves are one wave type which will propagate in a plate medium. In addition, although vertically polarized shear and longitudinal waves do not satisfy the plate boundary conditions individually, a combination of those two wave types will propagate in a combined form which is known as a Lamb wave. Two families of Lamb waves, antisymmetric and symmetric, can be generated in a plate-type medium.

Whatever wave type is utilized, an essential component in any ultrasonic testing system is a device which will effectively generate the desired ultrasonic waves. This function has frequently been accomplished in the past by piezoelectric transducers, which utilize the piezoelectric effect to convert electrical energy into the mechanical energy of wave motion. Piezoelectric transducers, however, require some form of mechanical contact with the material in which the waves are to be generated, and in many applications this requirement has limited the usefulness of such transducers.

A new family of ultrasonic transducers has recently been developed which offers significant operational advantages over the tranditional piezoelectric systems. These new transducers, known as electromagnetic acoustic transducers (EMATs) do not require any mechanical contact with the wave medium and are capable of operating at elevated temperatures and high speeds. An EMAT employs a coil of wire, which is driven at a dynamic frequency $\omega$, and a permanent or electromagnet, which is utilized to produce a static magnetic bias field $H_o$. When such an EMAT is placed near an electrically conductive material, ultrasonic waves are generated in the material as a result of the Lorentz body force $$F = \mu_o J_\omega \times H_o$$

where $J_\omega$ is the dynamic eddy current which is induced in the material by the coil of the EMAT. Furthermore, ultrasonic waves which are propagating in a material can be detected by the same type of transducer through the reciprocal process. The Lorentz mechanism by which such a transducer operates is familiar as the principle upon which the operation of an ordinary electric motor is based.

A variety of EMAT coil and magnet configurations have been developed to couple to particular elastic wave modes or polarizations. One of the most widely used EMAT transducer types, for example, is the meander coil EMAT transducer, examples of which are disclosed in U.S. Pat. Nos. 3,850,028 and 4,048,847, which are incorporated herein by reference. A meander coil transducer can be utilized to excite Rayleigh, Lamb, vertically polarized angle shear, or angle longitudinal ultrasonic waves, depending on the frequency at which the transducer is driven. In addition, when a meander coil transducer is equipped with an electromagnet, it can be adjusted to exert that static magnetic bias strength which provides maximum efficiency in ultrasonic wave generation.

Meander coil transducers have heretofore been employed to generate and detect ultrasonic waves used in testing for the presence of flaws in various materials. The wave types which typically are generated, however, such as Lamb waves, are subject to mode conversion when those waves are reflected from boundaries of the material or from flaws and other discontinuities in the material. Lamb waves, for example, will readily convert from the antisymmetric family to the symmetric family of Lamb waves. Because of this mode conversion effect, it has proven desirable in some applications to employ horizontally polarized shear waves, which are less subject to mode conversion, and thereby avoid spurious reflections and other coherent noise introduced by mode conversion. Horizontally polarized shear waves are more difficult to produce but may be generated and detected by another kind of EMAT, known as a permanent magnet EMAT. Typical examples of permanent magnet EMATs are disclosed in U.S. Pat. No. 4,127,035, which is incorporated herein by reference. Although there is thus available a transducer which is capable of generating and detecting horizontally polarized shear waves, the periodic magnet EMAT exhibits a number of operational disadvantages. When used on ferromagnetic materials, for example, such a transducer operates with a variable efficiency, which can introduce data interpretation problems. Furthermore, the design of the coil of such a transducer is such that a periodic magnet EMAT exhibits relatively high electrical losses relative to other transducer designs, such as the meander coil. Finally, the relatively high impedance of a periodic magnet EMAT makes it difficult to drive such a transducer with solid state circuitry. In addition, it is difficult to produce such an EMAT with an efficient directional radiation pattern, although unidirectional operation is sometimes necessary in particular applications.

Therefore, a need has developed for an improved transducer design which will generate or detect horizontally polarized shear waves.

In addition, a need has developed for a horizontally polarized shear wave transducer in which the magnetic bias may be varied in order to operate the transducer at maximum efficiency.

A need has also developed for a transducer which is capable of generating horizontally polarized shear waves in one direction in order to provide optimum utilization of the propagated wave energy.

Finally, a need has developed in the art for an improved transducer design which will generate horizontally polarized shear waves with a relatively low amount of electrical leakage from the transducer.

SUMMARY OF THE INVENTION

It is a general object of this invention to provide a new and improved apparatus and method for generating and detecting horizontally polarized ultrasonic shear waves in ferromagnetic materials.

A unidirectional electromagnetic acoustic transducer, according to the present invention, includes a first electrical conductor adapted to carry a first alternating current in a first current plane, the first current being conveyed by the first conductor at any instant in parallel and alternate directions spaced by a uniform amount, a second electrical conductor adapted to carry a second alternating current 90° out of phase with respect to the first alternating current in a second current plane substantially coplanar with the first current plane, the second current being conveyed by the second conductor at any instant in parallel and alternate directions spaced by the same uniform amount, the second conductor being parallel to but staggered from the first conductor by one half of the uniform amount, and a source of magnetic flux positioned to direct a static magnetic field parallel to the alternate directions, the transducer thereby being adapted to generate or detect a unidirectional horizontally polarized shear wave in a ferromagnetic material.

A method for generating a unidirectional horizontally polarized shear wave in a ferromagnetic material, according to the present invention, includes the steps of:

(a) establishing a static magnetic field parallel to a surface of the material, (b) constraining a first alternating current to follow a first uniformly spaced serpentine path predominantly parallel to the magnetic field and parallel to the surface of the material, and (c) constraining a second alternating current 90° shifted in phase with respect to the first current to follow a second serpentine path substantially coplanar with the first path and having the same uniform spacing but staggered from said first path by half the spacing distance.

The method may further include the step of adjusting the strength of the static magnetic field to achieve maximum efficiency in the generation of the horizontally polarized shear wave.

Examples of the more important features of the invention have been broadly outlined in this Summary in order to facilitate an understanding of the detailed description that follows, and so that the contributions which this invention provides to the art may be better appreciated. There are, of course, additional features of the invention, which will be further described below, and which are included within the subject matter of the appended claims.

BRIEF DESCRIPTION OF THE DRAWINGS

Additional objects, features, and advantages of the present invention will become apparent by referring to the detailed description below of the preferred embodiments in connection with the accompanying drawings, wherein like reference numerals refer to like elements throughout all the figures. In the drawings.

DESCRIPTION OF THE PREFERRED EMBODIMENT

Figure 1:
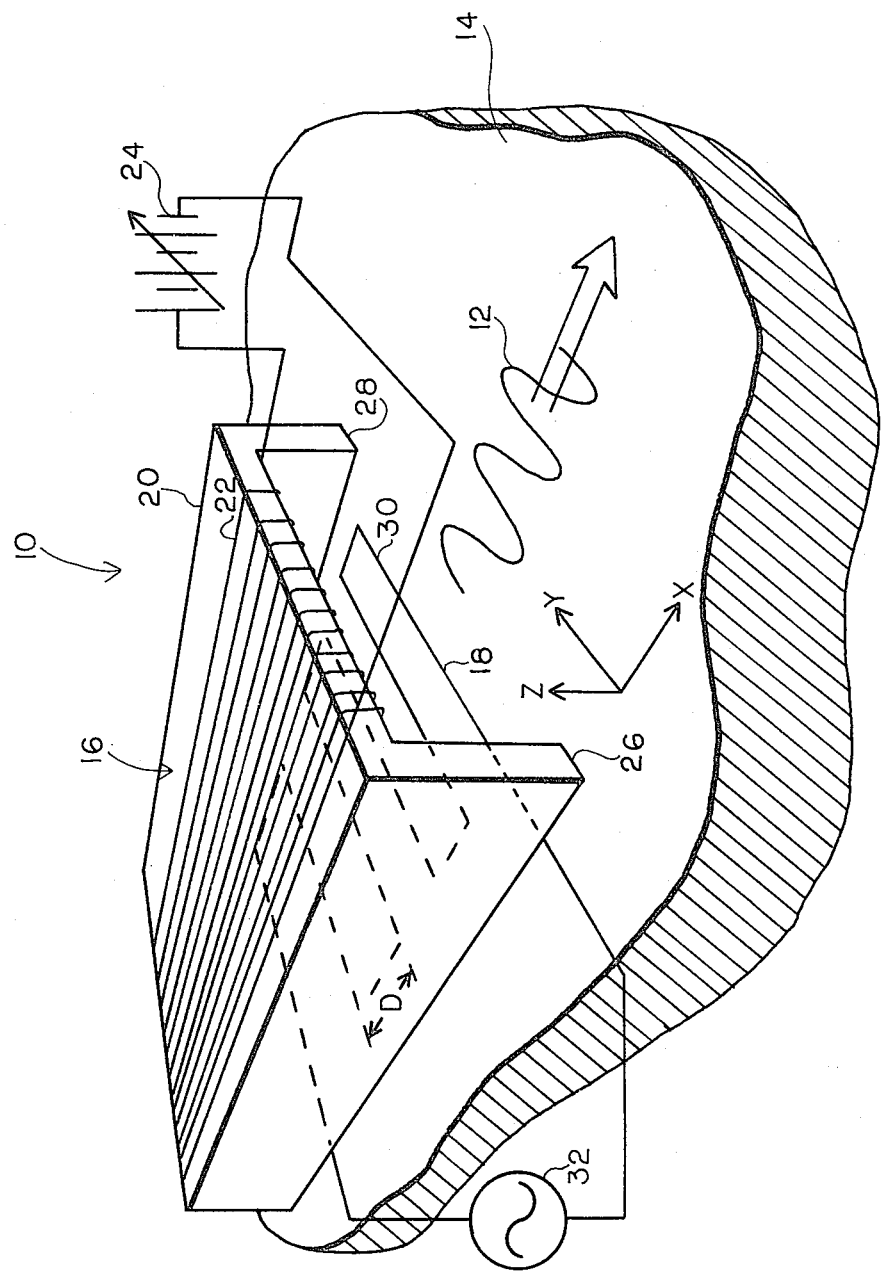
FIG. 1 is a perspective view of an electromagnetic acoustic transducer.

In FIG. 1, an electromagnetic acoustic transducer (EMAT) 10 is designed to generate a horizontally polarized shear wave 12 in a ferromagnetic material 14.

The basic components of the EMAT 10 are an electromagnet 16 and a meander coil 18. The electromagnet 16 includes a pole piece 20 and a coil 22. The coil is connected to a source of direct current 24, which may be adjusted to vary the amount of current supplied to the coil. The current passing through the coil 22 will produce a magnetic field which will lie generally in the y direction between the extensions 26 and 28 of the pole piece 20. The magnetic field strength may be varied by adjusting the source 24, for reasons which will be further discussed below.

The second major component of the electromagnet is the meander coil 18. The meander coil is composed of a number of parallel, uniformly spaced elements 30, which are connected in series and are positioned so that all the elements 30 lie in a common plane. In this manner, a dynamic magnetic field is created in the material 14. At any given instant, the dynamic magnetic field arising from the passage of current through the meander coil will be directed alternately in the + or −x direction, with a periodicity equal to twice the spacing D of the elements 30 in the coil 18.

The coil 18 in the EMAT of the present invention is positioned so that the elements 30 are parallel to the static magnetic field established by the magnet 16. With this configuration, the Lorentz forces which operate in other EMAT designs will not be generated, since the vector cross product of the static magnetic field and the current will be 0. Referring to the coordinate system as defined in FIG. 1, however, it can be seen that the resultant magnetic field caused by the EMAT 10 will consist of a dynamic component $H_x$ superimposed on a static bias component $H_{oy}$. In the high bias limit, where the ferromagnetic material 14 is close to saturation, the magnetization of the material will be changed by reversible rotations and will essentially follow the vector sum of these fields. The magnetization, therefore, will oscillate in the x-y plane about the y axis. In this limit, polycrystalline ferromagnetic materials, such as nickel and steel, tend to shorten in the direction of magnetization. As the field and the magnetization rotate, the material thus tends to shorten along their instantaneous direction. Consequently, a deformation or contraction of the material 14 is also rotating in the x-y plane. Under dynamic conditions, this effect may be described by stresses $\sigma_{xy}$ which, when coupled with the periodicity induced in the x direction by the meander coil, will produce an effective body force $f_y$ in accordance with the relation $$f_y = (\partial/\partial x)\, \sigma_{xy}.$$

The horizontally polarized shear waves are generated as a result of this force $f_y$.

Although FIG. 1 depicts the use of the transducer 10 to generate a wave, those skilled in the art will appreciate that the transducer 10 may also be employed to detect a horizontally polarized shear wave by a reciprocal process.

Figure 2A:
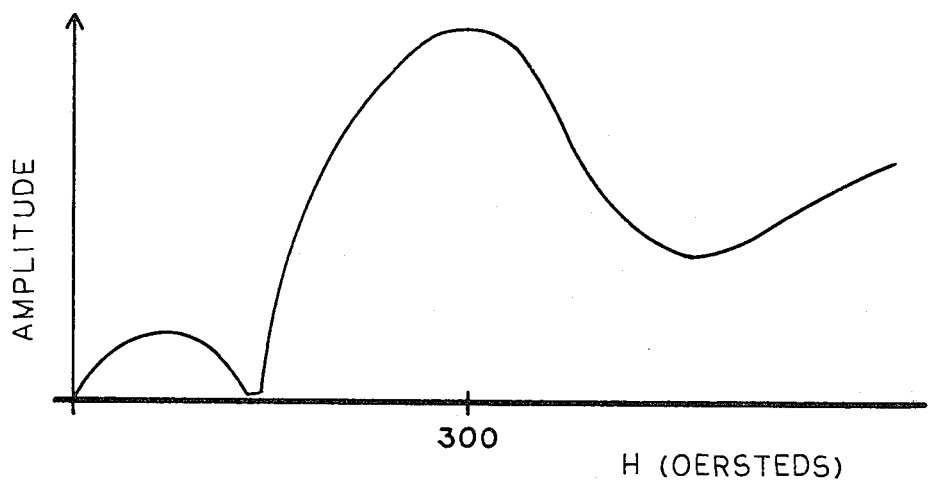
FIGS. 2A and 2B provide graphical representations indicating the ultrasonic wave amplitude generated as a function of bias field strength, for a prior art transducer and the transducer of FIG. 1.
Figure 2B:
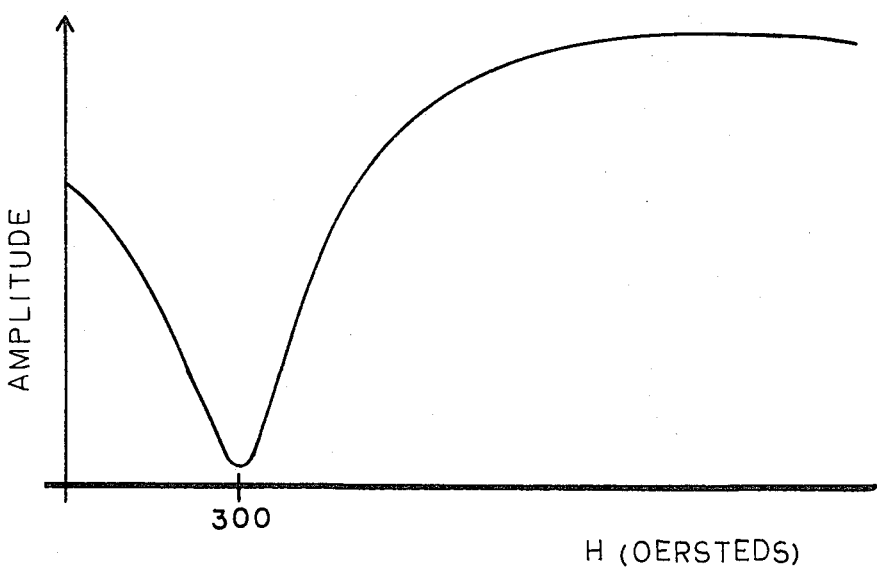

FIG. 2 provides a graphical representation illustrating experimental results which were obtained in an experimental comparison between a prior art transducer and the transducer of FIG. 1. FIG. 2A indicates the variation in amplitude which was measured for a fundamental mode antisymmetric Lamb wave transmitting between a pair of prior art meander coil transducers arranged with the static magnetic field perpendicular to the predominant direction of the meander coil, in 4130 steel plate. FIG. 2B illustrates the variation in the output signal amplitude for a fundamental mode horizontally polarized shear wave in 4130 steel utilizing transducers built according to the present invention. The signal generating frequency for FIG. 2B was higher than that for FIG. 2A, since a horizontally polarized shear wave travels faster than an antisymmetric Lamb wave. As can be seen from the shapes of the curves in FIGS. 2A and 2B, it is desirable to be provided with the capability to vary the static magnetic bias applied by a transducer in order to maximize the amplitude of the ultrasonic wave which is generated. In a transducer built according to FIG. 1, this adjustment may be accomplished by varying the DC source 24. Such an adjustment has not been possible before this invention for transducers capable of generating a horizontally polarized shear wave.

The present invention makes possible the generation or detection of horizontally polarized shear waves by a meander coil EMAT in ferromagnetic materials. The combination of a meander coil EMAT and the generation of horizontally polarized shear waves offers several significant advantages over previous ultrasonic generation techniques. Horizontally polarized shear waves are important in ultrasonic testing because they do not undergo a mode conversion when such waves strike surfaces parallel to their direction of polarization. Consequently, the resulting signals in horizontally polarized shear wave measurements are relatively simple and more easily processed.

Figure 3:
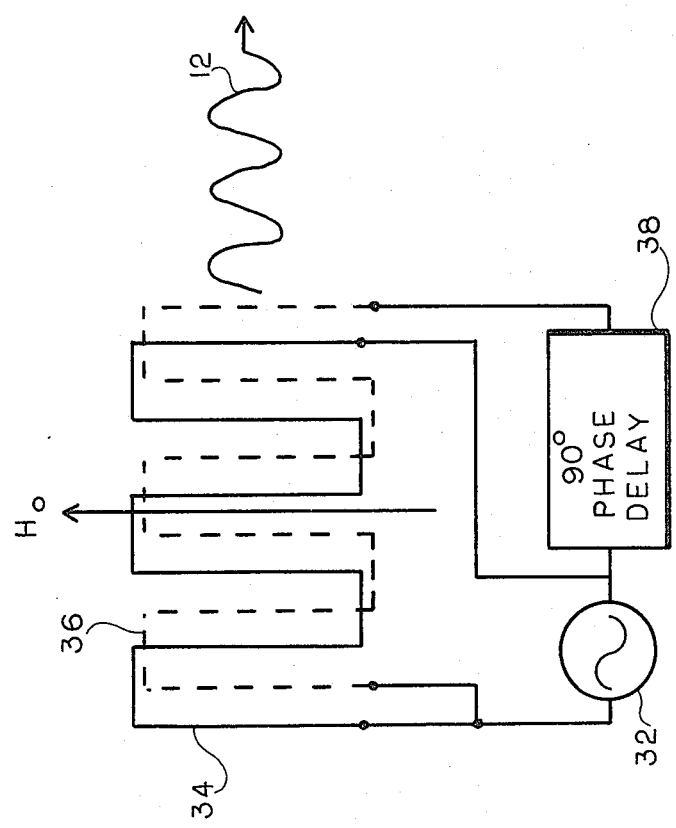
FIG. 3 is a schematic illustration depicting a unidirectional electromagnetic acoustic transducer constructed according to the present invention.

The use of a meander coil transducer also provides several important advantages over the periodic magnet transducer, which previously was the only transducer capable of generating or detecting horizontally polarized shear waves. The periodic magnet transducer exhibits a variable efficiency on ferromagnetic parts, characteristically high losses from electromagnetic radiation, and radiates wave energy in an undesirable spatial pattern. The meander coil design of this invention exhibits a lower impedance level which makes it easier to drive with solid state circuitry. Furthermore, the meander coil configuration does not strongly radiate electromagnetic energy, thereby reducing shielding and leakage problems. An additional disadvantage of the periodic magnet transducer is that it does not readily lend itself to unidirectional operation, which is frequently desirable in ultrasonic testing so that multiple signals can be avoided in detection systems. FIG. 3 provides a schematic illustration in an embodiment of the present invention which can be used to generate horizontally polarized shear waves in a single direction or, by the reciprocal process, to detect horizontally polarized shear waves travelling in one particular direction.

The transducer outlined in FIG. 3 is similar to that shown in FIG. 1, in that it employs a magnet to provide a static magnetic field $H_o$ which is oriented parallel to the predominant direction of the meander coil elements of the transducer. The EMAT of FIG. 3, however, employs two meander coils, a first meander coil 34 and a second meander coil 36, which is identical to the first meander coil, but is staggered from the first meander coil in the direction of the horizontally polarized shear wave propagation by one half the spacing of the meander coil elements. The first meander coil 34 is connected to a high frequency signal generator 32, similar to the arrangement in FIG. 1. The second meander coil 36, however, is connected to the signal generator 32 through a 90° phase delay 38. Due to the combination of the physical displacement between the two coils 34 and 36, and the 90° phase difference between the signals provided to the two coils, the forces exerted on a ferromagnetic material by the two coils will be additive for waves propagating in one direction and will cancel each other for wave propagating in the other direction, with the result that a horizontally polarized shear wave 12 is propagated in one direction only.

In conclusion, although typical embodiments of the present invention have been illustrated and discussed herein, numerous modifications and alternative embodiments of the apparatus and method of this invention will be apparent to those skilled in the art in view of this description. Accordingly, this description is to be considered as illustrative only and is provided for the purpose of teaching those skilled in the art the manner of constructing the apparatus and performing the method of this invention. Furthermore, it should be understood that the forms of the invention depicted and described herein are to be considered as the presently preferred embodiments. Various changes may be made in the configurations, sizes, and arrangements of the components of the invention, as will be recognized by those skilled in the art, without departing from the scope of the invention. Equivalent elements, for example, might be substituted for those illustrated and described herein, parts or connections might be reversed or otherwise interchanged, and certain features of the invention might be utilized independently of the use of other features, all as will be apparent to one skilled in the art after receiving the benefit obtained through reading the above description of the invention.

What is claimed is:

1. A unidirectional electromagnetic acoustic transducer, comprising:
a first electrical conductor adapted to carry a first alternating current in a first current plane, said first current being conveyed by said first conductor at any instant in parallel and alternate directions spaced by a uniform amount;
a second electrical conductor adapted to carry a second alternating current 90° out of phase with respect to said first alternating current in a second current plane substantially coplanar with said first current plane, said second current being conveyed by said second conductor at any instant in parallel and alternate directions spaced by said uniform amount, said second conductor being parallel to but staggered from said first conductor by one half said uniform amount; and a source of magnetic flux positioned to direct a static magnetic field parallel to said alternate directions.

2. The transducer of claim 1, wherein said first transducer comprises a first meander coil and said second transducer comprises a second meander coil.

3. The transducer of claim 2, wherein said first meander coil comprises:
a first plurality of parallel, uniformly spaced elements connected in series; and
a second meander coil comprises a second plurality of parallel, uniformly spaced elements connected in series,
said first and second coils thereby forming first and second conduction paths for said first and second currents, respectively.

4. The transducer of claim 1, wherein said magnetic flux source comprises an electromagnet, thereby affording adjustment of said static magnetic bias.

5. The transducer of claim 4, further comprising a high frequency signal generator adapted to supply said alternating current to said conductor.

6. A unidirectional electromagnetic acoustic transducer, comprising:
a first meander coil;
a high frequency signal generator driving said first coil;
a second meander coil having the same period as said first coil, positioned parallel to and coplanar with said first coil but offset from said first coil by one fourth of said period;
a 90° phase shifter receiving the output of said signal generator and driving said second meander coil; and
a magnet positioned to produce a static magnetic field parallel to the predominant current carrying direction of said coils,
said transducer thereby being adapted to generate a unidirectional horizontally polarized shear wave in a ferromagnetic material.

7. A unidirectional electromagnetic acoustic transducer, comprising:
means for establishing a static magnetic field parallel to a surface of a ferromagnetic material;
means for constraining a first alternating current to follow a first uniformly spaced serpentine path predominantly parallel to said magnetic field and parallel to said surface; and
means for constraining a second alternating current, 90° shifted in phase with respect to said first current, to follow a second serpentine path substantially coplanar with said first path and having the same uniform spacing but staggered from said first path by one half said spacing distance.

8. A method for generating a unidirectional horizontally polarized shear wave in a ferromagnetic material, comprising the steps of:
establishing a static magnetic field parallel to a surface of the material;
constraining a first alternating current to follow a first uniformly spaced serpentine path predominantly parallel to the magnetic field and parallel to the surface of the material; and
constraining a second alternating current 90° shifted in phase with respect to the first current to follow a second serpentine path substantially coplanar with the first path and having the same uniform spacing but staggered from said first path by one half the spacing distance.

9. The method of claim 8, further comprising the step of adjusting the strength of the static magnetic field to achieve maximum efficiency in the generation of the horizontally polarized shear wave.

* * * * *